United States Patent [19]  
Pestellini et al.

[11] 4,372,958  
[45] Feb. 8, 1983

[54] COMPOUND HAVING ANTITUSSIVE ACTIVITY

[75] Inventors: Vittorio Pestellini; Mario Ghelardoni, both of Florence; Danilo Giannotti, Lucca; Alberto Meli; Carlo A. Maggi, both of Florence, all of Italy

[73] Assignee: A. Menarini S.A.S., Italy

[21] Appl. No.: 272,281

[22] Filed: Jun. 10, 1981

[30] Foreign Application Priority Data

Feb. 25, 1981 [IT]  Italy .................................. 9343 A/81

[51] Int. Cl.³ ..................... A61K 31/52; C07D 473/08
[52] U.S. Cl. .................................. 424/253; 544/267; 544/394
[58] Field of Search ....................... 544/267, 394, 270; 424/253

[56]        References Cited  
U.S. PATENT DOCUMENTS 3,163,649 12/1964 Morren ............................... 544/394  
3,352,864 11/1967 Guiroy ................................ 544/267

Primary Examiner—Paul M. Coughlan, Jr.  
Attorney, Agent, or Firm—McGlew and Tuttle

[57]            ABSTRACT

A new compound 3(4-phenyl-1-piperazinio-1-yl)-1,2-propanediol 3(theophyllin-7-yl)-1-propanesulphonate, possesses antitussive action and is therefore usable in therapy. The compound is obtained by treating 3(theophyllin-7-yl)-1-propanesulphonic acid with 3(4-phenyl-piperazin-1-yl)-1,2-propanediol in a suitable solvent.

4 Claims, No Drawings

COMPOUND HAVING ANTITUSSIVE ACTIVITY

BACKGROUND OF THE INVENTION

1. Field of the Invention

This invention relates to a new compound having antitussive activity and to a process for the preparation of the compound and its application in therapy.

2. Description of the Prior Art

The antitussive action of 3(4-phenylpiperazin-1-yl)-1,2-propanediol is documented (P. R. B. Noel, ARZN, FORSCH. 19 (8) 1246 (1969); Cartwright T. K., Paterson J. H., J. PHARM. PHARMACOL. 23 (Suppl.) 247 S (1971)). However, its use is limited, particularly in the case of parenteral administration, because of its toxicity and the side-effects which it has on the cardiocirculatory system.

SUMMARY OF THE INVENTION

According to the invention, there is provided 3(4-phenyl-1-piperazinio-1-yl)-1,2-propanediol 3(theophyllin-7-yl)-1-propane-sulphonate, which corresponds to the following structural formula (I):

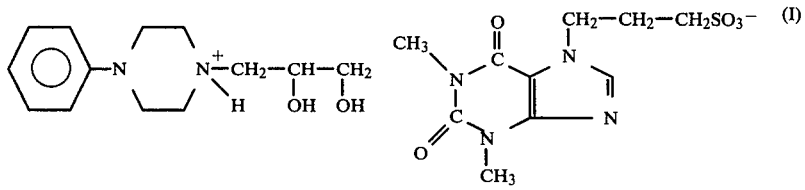

The compound I is in the form of a white crystalline powder of M.P. 160°–162° C., which is very soluble in water (greater than 20%) and stable in aqueous solution.

The invention also relates to the application of 3(4-phenyl-1-piperazinio-1-yl)-1,2-propanediol 3(theophyllin-7-yl)-1-propane-sulphonate (I) in human therapy, as this product possesses antitussive activity. In this respect, it has been shown pharmacologically that the 3(4-phenyl-1-piperazinio-1-yl)-1,2-propanediol 3(theophyllin-7-yl)-1-propanesulphonate (I) possesses, for equal doses, a toxicity which is distinctly less than that of 3(4-phenylpiperazin-1-yl)-1,2-propanediol, coupled with an equal or greater pharmacological activity in the antitussive sense and lesser effect on the cardiocirculatory system.

The present invention also relates to the preparation of compound I by treating 3(theophyllin-7-yl)-1-propanesulphonic acid with 3(4-phenylpiperazin-1-yl)-1,2-propanediol in a suitable solvent.

DESCRIPTION OF THE PREFERRED EMBODIMENT

The following method of preparation is described by way of non-limiting example:

30.1 g (0.1 moles) of 3(theophyllin-7-yl)-1-propanesulphonic acid are added under stirring to 23.7 g (0.1 moles) of 3(4-phenylpiperazin-1-yl)-1,2-propanediol in 2500 ml of ethyl alcohol. The mixture is heated until boiling, the solution is filtered while hot and is allowed to cool. The resultant precipitate of the desired compound I is filtered and crystallized repeatedly from ethanol, to give a M.P. of 160°–162° C.

Absorption maxima in aqueous solution at 233 nm ($\epsilon=21,000$) and at 274 nm ($\epsilon=28,000$).

Pharmaco-toxicological experiments on the compound I led to the following conclusions.

The acute toxicity by oral and subcutaneous administration in the male and female mouse of 3(4-phenyl-1-piperazinio-1-yl)-1,2-propanediol 3(theophyllin-7-yl)-1-propanesulphonate (I) in comparison with those of 3(4-phenylpiperazin-1-yl)-1,2-propanediol (II) is shown in Table I.

TABLE I

| | DL 50 expressed in g/kg of body weight with 95% reliability limits | | | |
|---|---|---|---|---|
| COM- | ORAL | | SUBCUTANEOUS | |
| POUND | MALE | FEMALE | MALE | FEMALE |
| I | 1.43 | 1.59 | greater than 1.5 | |
| | (1.00–1.87) | (1.11–2.29) | | |
| II | 0.67 | 0.62 | 0.76 | 0.72 |
| | (0.65–0.69) | (0.43–0.90) | (0.40–1.43) | (0.42–1.22) |

I: 3(4-phenyl-1-piperazinio-1-yl)-1,2-propanediol 3(theophyllin-7-yl)-1-propanesulphonate
II: 3(4-phenylpiperazin-1-yl)-1,2-propanediol The antitussive action was evaluated by the citric acid aerosol test on the guinea-pig (Iolanpaan-Hekkila J. E. Jalonen, K. Vartiainen, A.Acta Pharmac. 25, 333 (1967)). By administering equiponderal doses orally and subcutaneously, the antitussive action of compound I was found to be respectively equal to and 1.5 times greater than that of compound II.

Because of its lower acute toxicity, compound I therefore has a much more favourable therapeutic index than compound II.

The side-effects on the cardiocirculatory system by compound I compared with compound II were studied in the anaesthetised rat after intravenously administering a dose of 2.5 mg/kg of body weight. After 15 minutes from its administration, compound II causes a significant reduction, to the extent of 20–30%, in the systolic pressure, diastolic pressure and cardiac frequency, whereas at the same dose and over the same time period compound I causes no significant variations with respect to the controls.

The compound according to the invention is used in human therapy at doses of between 10 mg and 500 mg, and is presented in the form of dosage units such as phials, droplets, tablets, capsules, suppositories or aerosols, where necessary together with a suitable carrier or excipient.

What is claimed is:

1. 3(4-phenyl-1-piperazinio-1-yl)-1,2-propanediol 3(theophyllin-7-yl)-1-propanesulphonate.

2. A drug having antitussive action which contains an antitussive effective amount of the compound 3 (4-phenyl-1-piperazinio-1-yl)-1,2-propanediol 3(theophyllin-7-yl)-1-propanesulphonate.

3. A drug according to claim 2, in dosage unit form useable in human therapy and containing said compound in an antitussive effective unit dosage of between 10 mg and 500 mg.

4. A method of treating a patient to obtain antitussive relief from coughing which comprises administering to the patient a drug according to claim 2.